United States Patent [19]

Pfefferkorn

[11] Patent Number: 5,401,640

[45] Date of Patent: Mar. 28, 1995

[54] METHOD FOR ENHANCING DETECTION OF SUPEROXIDE ANION

[75] Inventor: Lorraine C. Pfefferkorn, Hanover, N.H.

[73] Assignee: Trustees of Dartmouth College, Hanover, N.H.

[21] Appl. No.: 859,891

[22] Filed: Mar. 30, 1992

[51] Int. Cl.$^6$ .......................... C12Q 1/28; G01N 21/76
[52] U.S. Cl. ........................................... 435/28; 435/4; 435/29; 435/810; 422/52; 422/61; 436/172; 436/808
[58] Field of Search ............................ 435/29, 28, 810; 422/52, 61; 436/172, 808

[56] References Cited

U.S. PATENT DOCUMENTS

| | | | |
|---|---|---|---|
| 4,598,044 | 7/1986 | Kricka et al. | 435/28 |
| 4,729,950 | 3/1988 | Kricka et al. | 435/28 |
| 4,835,101 | 5/1989 | Kao et al. | 435/28 |
| 4,842,997 | 6/1989 | Carter et al. | 435/6 |
| 4,959,182 | 9/1990 | Schaap | 252/700 |
| 4,962,192 | 10/1990 | Schaap | 536/18.1 |

OTHER PUBLICATIONS

US Patent & Trademark Translation of "New Chemiluminescent Reaction of Luminol in the Presence of Vanadium Salts", Pilipenko et al, Ukr. Khim Zh. (Russ. ed) 39 (1); 73–5, 1973.

Robbins et al; "Basic Pathology"; 4th ed.; 1987; pp. 35–36; W. B. Sanders Company. Phil. Pa.

Liochev, S. I., Fridovich, I. (1989) *Arch. Biochem. Biophys.* 275, 40–43.

Yoshino, S. Sullivan, S. G. and Stern, A. (1989) *Arch. Biochem. Biophys.* 272, 76–80.

Coulombe, R. A. Jr., Briskin, D. P., Keller, R. J., Thornley, W. R. and Sharma, R. P. (1987) *Arch. Biochem. Biophys.* 255, 267–273.

Reif, D. W., Coulombe, R. A. Jr., and Aust, S. D. (1989) *Arch. Biochem. Biophys.* 270, 137–143.

Rau, M., Patole, M. S., Jihaya, S., Ramakrishna Kurup, C. K., and Ramasarma, T. (1987) *Mol. Cell Biochem.* 75, 151–159.

Liochev, S., Ivancheva, E., and Fridovich, I. (1989) *Arch. Biochem. Biophys.* 269, 188–193.

*Primary Examiner*—Robert J. Warden
*Assistant Examiner*—Hien Tran
*Attorney, Agent, or Firm*—Lahive & Cockfield, Guilio A. DeConti, Jr.

[57] ABSTRACT

A method for enhancing luminol chemiluminescence assays for superoxide anion comprising an orthovanadate salt, such as sodium orthovanadate. Orthovanadate enhances photon emission when luminol is cleaved by superoxide anion. The orthovanadate salt is non-cytotoxic and non-denaturing to intact cells. A method comprises reacting luminol in the presence of an orthovanadate anion with an analyte suspected of containing superoxide anion and measuring the photon output. A kit comprises a predetermined amount of luminol and orthovanadate in separate containers.

16 Claims, 3 Drawing Sheets

METHOD FOR ENHANCING DETECTION OF SUPEROXIDE ANION

FIELD OF THE INVENTION

The present invention relates to a composition and method for enhancing detection of superoxide anion in a luminol chemiluminescence assay.

BACKGROUND OF THE INVENTION

Superoxide anion is a short-lived oxygen radical released to the outside of appropriately stimulated leukocytes (monocytes, macrophages, and polymorphonuclear leukocytes). Synthesis involves a cytochrome b 558-containing plasma membrane enzyme complex called NADPH oxidase which transfers an electron to molecular oxygen, thus radicalizing it. The short-lived superoxide anion is a potent oxidant and can damage infectious organisms not protected by a countering superoxide-dismutation enzyme or scavenger. The dismutation product, hydrogen peroxide, is also toxic to a range of organisms.

As a front line immunologic response to infections, the importance of oxygen radical release to immunity is demonstrated in people who suffer from chronic granulomatous disease (CGD). These people lack NADPH oxidase activity. Without medical intervention, they suffer life threatening crises from infections that are normally controlled through this immune response. CGD is a disease caused by known genetic defects in components of the oxidase-excitation pathway. People with CGD have normal cell-mediated and humoral immunity; only their oxidase activity is defective. Theirs is a form of immunologic deficiency that is so specific in its cause that it clearly identifies the contribution of oxygen radicals to innate disease control.

The study of cellular pathways that activate the NADPH oxidase, and the components that comprise it, have received considerable attention in recent years. Ongoing projects are in the interests of basic science as well as of clinical research. At present, the methods most often used for detecting superoxide include measurements of: (1) the reduction of exogenously supplied cytochrome c; (2) uptake of oxygen from the medium (measured by the Clark electrode); and, (3) luminol-mediated chemiluminescence. The first method has limited sensitivity, and is complicated by the reoxidation of superoxide-reduced cytochrome c by contaminants and cell lysis. The oxygen uptake method is less sensitive than cytochrome c reduction and has the serious disadvantage of requiring prohibitively large numbers of cells per assay. The third method, luminol-mediated chemiluminescence, is more sensitive than the other two, With accurate readings extending over a range of signal spanning three orders of magnitude.

Luminol chemiluminescence assay measurement involves the measurement of superoxide anion produced by cell biochemistry. For the purposes of the present invention, luminol will also include a related variation known as isoluminol. Discussion of luminol is intended to include isoluminol. The chain of events is believed to involve cell surface receptors, such as those binding complexed immunoglobulin G (Fc receptors) or bacterial formylated peptides (f-met-leu-phe receptors), which are stimulated by their specific agonists. Any means for signal transduction to activate NADPH oxidase is usable with the assay of the present invention. Such means can be physiologic or mimetic of the physiologic pathway.

The activated receptor triggers the production or activation of NADPH oxidase, which binds to and radicalizes molecular oxygen by adding an electron. The radicalized oxygen, called superoxide anion, is subsequently released into the extracellular environment, where it can interact with luminol. Superoxide anion by itself oxidizes available lipid and proteins some of which chemiluminesce as a result. This type of chemiluminescence produces a very poor, inefficient means of measuring superoxide artion. However, the addition of luminol results in an amplified signal with a proportionality to superoxide produced by the cells.

Luminol chemiluminescence assay functions as a detection and measurement technique because of the ability of superoxide anion to cleave luminol. This cleavage results in the release of photons (light), which can be measured by a luminometer, or other appropriate instrument. It is estimated that the photon to superoxide ratio is 1:1000.

It would be advantageous to enhance the sensitivity of the chemiluminescence assay in order to more accurately detect or measure lower concentrations of superoxide artion than currently possible. Enhancement of the photon signal in an assay with a concentration of superoxide anion present would be desirable.

U.S. Pat. Nos. 4,949,182, issued Sep. 25, 1990, and 4,962,192, issued Oct. 9, 1990, both to Schaap, disclose light producing compounds and compositions providing enhanced chemiluminescence. The compounds disclosed are 1,2-dioxetanes of various structures, which can be triggered to produce light at room temperatures when cleaved by an activating agent. U.S. Pat. No. 4,835,101, issued to Kao et al., discloses a reagent for luminescence-monitored enzyme assays containing an enhancer of 4-iodophenol or 4-phenylphenol. U.S. Pat. No. 4,598,044, issued to Whitehead et al., discloses a phenolic derivative as an enhancer. U.S. Pat. No. 4,842,997, issued to Carter et al., discloses the use of 6-hydroxybenzothiazole.

Kits containing luminol-enhancement reagents for performing chemiluminescence assays are commercially available from companies such as U.S. Biochemicals, Amersham and BioRad as non-isotopic detection systems for Western and DNA blotting. Some enhancement reagents use phenolic-based compounds, such as iodophenol. However, such enhancers are toxic to live cells and denaturing to some components of subcellular systems and cannot be used for in situ assays. It would be desirable to have an enhancement reagent that is non-cytotoxic and that does not denature components for use in assaying the activity of live cells.

SUMMARY OF THE INVENTION

Accordingly, the present invention provide a composition and method for a non-cytotoxic, non-stimulatory, and non-denaturing means of enhancement of luminol chemiluminescence assays. More particularly, the present invention comprises composition for chemiluminescence assay enhancement comprising an orthovanadate salt. In a preferred embodiment, the reagent is sodium orthovanadate.

The present invention further provides a method for performing a luminol-enhanced chemiluminescence assay comprising (a) providing an analyte suspected of containing superoxide anion; (b) providing an effective amount of luminol; (c) providing an effective amount of orthovanadate; (d) contacting the analyte with the luminol in the presence of orthovanadate in such a manner as to permit reaction of any superoxide present in the analyte with the luminol resulting in the chemical cleavage of luminol and the release of photons; and, (e) measuring the photons released in step (d).

The present invention further provides a kit for performing a luminol-enhanced chemiluminescence assay comprising an effective amount of orthovanadate and an effective amount of luminol. Either or both components can be in aqueous solution, or provided in solid form.

It is therefore a principal object of the present invention to provide a composition for enhancing a luminol chemiluminescence assay.

It is a further object of the present invention to provide a non-cytotoxic, non-stimulatory, and non-denaturing enhancing compound for enhancing the detection of superoxide anion produced by live cells.

It is yet a further object of the present invention to provide a compound comprising sodium orthovanadate for enhancing detection of superoxide anion in a luminol based chemiluminescence assay.

It is another object of the present invention to provide a non-cytotoxic method for the detection of superoxide anion intracellularly.

It is still another object of the present invention to provide a kit containing orthovanadate and luminol for performing an enhanced luminol chemiluminescence assay.

DESCRIPTION OF THE INVENTION

In general, the present invention relates to a compound useful for enhancing photon output in chemiluminescence assays, comprising an orthovanadate salt, such as sodium, potassium or other typical ionizable cation. In a preferred embodiment sodium orthovanadate is used. In a typical luminol chemiluminescence assay for superoxide anion, a preparation of cells in a biological medium is provided. The cells are suspected of containing an analyte of interest that can generate superoxide anion. The analyte can be any biological cell or cell fragment, an organelle, or a molecule or aggregation of molecules that can generate superoxide anion. Such cells include, but are not limited to, polymorphonuclear nucleocytes, the monocyte portion thereof, phagocytes, monocytic tumor cells, and the like.

A solution containing luminol and orthovanadate ion is added under appropriate conditions. Superoxide anion produced by a surface-membrane enzyme is released outside of the cell and reacts with luminol, resulting in cleavage of luminol. Each molecule of cleaved luminol results in the release of a photon. Emitted photons are measurable by any conventional spectrophotometer or luminometer.

While the mechanism of action of orthovanadate is not completely understood, it is believed that orthovanadate may act as an electron transporter, accepting an electron from the superoxide anion, being reduced in the process. An intermediate unstable vanadyl structure is formed during the transfer which then in turn transfers an electron to luminol, causing the cleavage and concomitant generation of photons. An alternative theory of the mechanism of action is that orthovanadate lowers the energy of activation for luminol cleavage, thereby catalyzing luminol cleavage.

Figure 1:
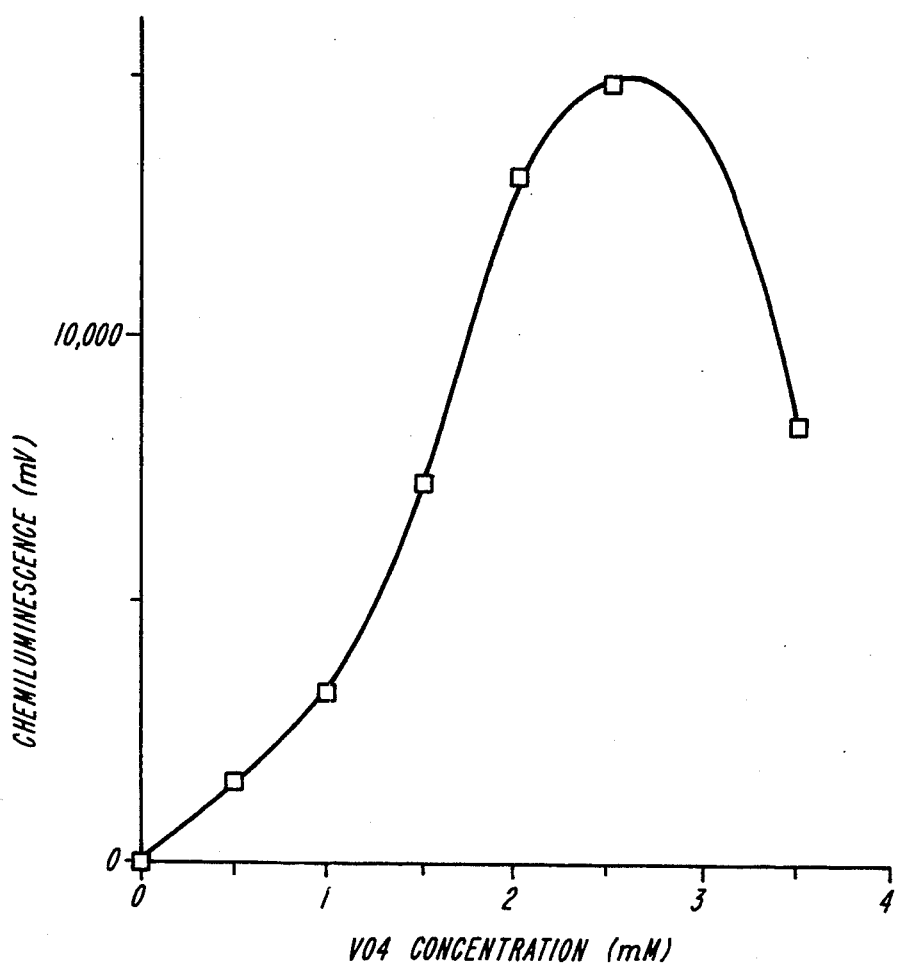
FIG. 1 is a graph showing the effect of orthovanadate concentration on superoxide anion dependent luminol chemiluminescence.

The effective concentration of orthovanadate is in the range of 0.01–2.5 mM. However, pH effects may have an effect on enhancement at the upper end of the concentration range. FIG. 1 illustrates the change in enhancement as orthovanadate concentration is increased. In a preferred embodiment, the concentration of orthovanadate is from 1.0–2.0 mM. See the Examples set forth hereinbelow for a detailed discussion.

The effect of orthovanadate on enhancement of chemiluminescent measurement is to increase sensitivity of the assay by approximately two orders of magnitude. Thus, the assay of the present invention can detect over 100 fold lower concentrations of superoxide anion than currently possible.

In the absence of a stimulus of superoxide anion, orthovanadate does not stimulate cells to generate superoxide anion, nor does it cause significant cleavage of luminol by itself. Therefore, orthovanadate enhancement is apparent only when cells are stimulated to produce superoxide anion. Orthovanadate enhances the detection of superoxide anion regardless of the means by which cells are stimulated. In addition to ligands that crosslink Fc receptors, superoxide anion production is triggered by phorbol myristate acetate (PMA) and formyl-methionyl-leucyl-phenylalanine (fMLP). Similar to Fc receptor stimulation, the detection of superoxide anion produced in response to these other stimulants is enhanced by orthovanadate. Furthermore, orthovanadate has been shown to enhance the detection of all tested sources of superoxide anion. Since orthovanadate enhancement of the detection of superoxide anion is not specific to a particular stimulant or cell type, it can be regarded as a general means of enhancing the detection of superoxide anion.

The method of the present invention comprises providing any analyte suspected of containing or of being able to generate superoxide anion, and contacting the analyte with an effective amount of luminol and orthovanadate. If superoxide anion is present, luminol will be cleaved and photons will be emitted. The photon emission can be measured by any standard spectrophotometer or similar detection instrument. A significant advantage of the present invention is the enhancement of the photon signal output over that of unenhanced luminol assay. As shown in the Examples below, enhancement of 500 fold increase is possible.

Another advantage of the present invention is the fact that orthovanadate is non-cytotoxic and is non-denaturing. All other known enhancers, such as phenolic compounds, are cytotoxic or denaturing, thus preventing their use on whole cell or biochemical cell assays.

The present invention provides a kit for performing luminol-enhanced chemiluminescent assays comprising an aqueous solution of luminol and an aqueous solution of sodium orthovanadate. Alternatively, a kit may be provided which comprises a single aqueous solution of luminol and sodium orthovanadate. The solutions may be provided in concentrated solutions, which are diluted by the user. Effective concentrations of the sodium orthovanadate are as disclosed hereinabove. It is also within the scope of the present invention for either or both of the components to be provided in solid or powdered form.

The assay of the present invention can be incorporated into a panel or battery of assays to monitor progress of drug or other therapy for a number of different analytes.

The assay of the present invention has a number of applications. The assay can be used for clinical assessment of leukocytes of patients who have altered oxidative means to control infections, and for biomedical research involving the analysis of leukocyte signal transduction pathways, components comprising the NADPH oxidase, and the requirements of the respiratory burst (superoxide generation). An example of this type of application is in the treatment of patients with chronic granulomatous disease (CGD), who lack the capacity to generate superoxide. Gamma interferon induces some components of the oxidase and gives some of the patients partial restoration of oxidase activity. This treatment involves repeated testing of their blood leukocytes, and it is clear that an enhanced detection system would mean that fewer cells could be taken for monitoring their treatment. In addition, the study of the capacity of AIDS patients to generate oxygen radical and to control opportunistic infections will be of growing importance for the foreseeable future.

Applications may be extended to the detection of cytosolic oxidases, or to any measurement of in-situ electron transfer that can be coupled to luminol excitation. Applications may also include in vitro systems whereby superoxide anion (or other appropriate electron donor such as any flavoprotein or cytochrome-containing protein or radicalized protein or AND(P)H that can be oxidized by orthovanadate or that can interact with the orthovanadate/luminol complex) is produced by exogenously-supplied superoxide-generating enzymes (or by other chemical reactions or enzyme systems).

The use of an enhanced detection kit need not be limited to investigations of leukocytes. Any detection system capable of producing superoxide, such as the binding of horseradish peroxidase-conjugated antibodies (commonly applied to Western blot techniques) or xanthine oxidase-conjugated antibodies (which require only xanthine to generate superoxide) to live cells, would produce oxygen radicals detectable by enhanced chemiluminescence. In these cases, antibodies would be identifying non-denatured antigens on cells. The enhancer of the present invention would increase the sensitivity of detection without involving cell death. Such cells could be isolated by a cell sorter, on the basis of emitted light, and then grown for further study. This would be far more sensitive than the present methods using fluorescein-labelled antibody, and could be achieved by simple changes in emission filters on current instruments.

Since the mechanism of superoxide detection by enhanced luminol chemiluminescence is the same regardless of the source of the superoxide, it is also possible to use the orthovanadate of the present invention in the study of intracellular superoxide-generating oxidases, such as those involved in liver detoxification. To specifically measure intracellular superoxide production, luminol/orthovanadate would be used to specifically measure superoxide anion production by these oxidases. Possible uses include drug metabolite monitoring, mitochondrial superoxide detection, cell aging and damage measurement due to superoxide that has escaped scavenging by superoxide dismutase.

Activity of phagocytes in the body may function as a measure of the severity and may be an indicator of change in condition in common disease states such as asthma and psoriasis. Routine monitoring of patients using enhanced chemiluminescence assays may detect subclinical activity which precludes clinical manifestation, thereby allowing monitoring of the treatment during therapy. Similarly, the present invention can be used to diagnose and monitor chronic inflammation disorders involving the entire pulmonary parenchyma which, if unchecked, can ultimately lead to fibrotic degeneration. Antioxidant and beta-agonistic therapy can be monitored during acute inflammation attacks such as pancreatitis. In the case of immunosuppressive disorders, whether due to disease (e.g., AIDS) or drug therapy (e.g., following transplant), enhanced chemiluminescence is superior to conventional methods for assessing phagocyte activity in that it not only determines cell numbers, but also gives an indication of the "healthiness" (the ability to produce superoxide) of the cell. Measurement of stimulation of chemiluminescence by opsonized bacteria and other micro-organisms could indicated a heightened immune state, possibly due to infection.

Moreover, other cell free systems considered for testing might include enzyme-linked immunosorbent assays (ELISA) that require non-denaturing conditions for antibody recognition, or that would benefit from a marked increase in sensitivity. The enhancer of the present invention is stable, and may be linkable to existing methods.

It may also be possible to use the present invention as a reporter gene. Currently, reporter genes are used by researchers to determine whether transfection has occurred in recombinant DNA techniques, or whether the promoter involved can turn on the transfected gene sequence. Luciferin/luciferase system is currently the most sensitive detection assay. However, it requires large numbers of cells. There is a need for greater sensitivity in the assay for gene protein. It may be possible to substitute xanthine oxidase as the reporter gene and luminol as the signal generating system. In such an assay, xanthine oxidase would take the place of NADPH oxidase as the component that generates superoxide anion. The presence of xanthine oxidase would be detected, upon addition of xanthine, by the production of superoxide anion. Addition of luminol and orthovanadate would generate an enhanced signal that is conveniently measured by a luminometer. This assay might have the advantage of increasing the detection of the reporter gene, and therefore of gene transfection and promotion.

The present invention can be used in agricultural testing to detect, measure or monitor,cell aging or damage in selected crops. Cell damage caused by pesticides or environmental pollution can be monitored to maintain appropriate levels or warn of dangerously high levels of cell damage.

The invention will be further described in connection with the following examples which are set forth for purposes of illustration only. The apparatus and techniques used in the preparation of reagents and/or performance or evaluation of the method of this invention are standard or as hereinbefore described.

EXAMPLES

Abbreviations used:

fMLP is formyl methionyl leucyl phenylalanine, a peptide for which there are receptors on monocytic cell surfaces, and a well known stimulant of NADPH oxidase activity.

mAb 197 is a monoclonal antibody that binds two different sites on FcRI and crosslinks these receptors, and is a known stimulant of NADPH activity.

PMA is phorbol myristate acetate, activator of an intracellular enzyme, protein kinase C, and a potent stimulant of NADPH oxidase activity.

$O_2^-$ is superoxide anion.

$VO_4^{-3}$ is orthovanadate anion.

mVolts (mV) represents the respiratory burst.

Example 1

FIG. 1 shows a graph of the effect of $VO_4^{-3}$ on $O_2^-$ dependent luminol chemiluminescence. The sodium salt of $VO_4^{-3}$ was used in this and the other Examples. $O_2^-$ production was stimulated by the addition of mAb 197 which crosslinks FcRI on monocytic cells. Crosslinked FcRI stimulated the generation of $O^-$. Unstimulated control cells did not generate $O_2^-$. Data in TABLE 1 (expressed in FIG. 1) is representative of four experiments.

TABLE 1

| $VO_4^{-3}$ (mM) | mVolts | Enhancement (multiple) |
|---|---|---|
| ($O_2^-$ present) | | |
| 0.0 | 20 | — |
| 0.5 | 1562 | 78 |
| 1.0 | 3266 | 163 |
| 1.5 | 7271 | 364 |
| 2.0 | 13124 | 656 |
| 2.5 | 14875 | 744 |
| ($O_2^-$ absent) | | |
| 0.0 | 0 | — |
| 1.0 | 17 | — |

Example 2

Figure 2:
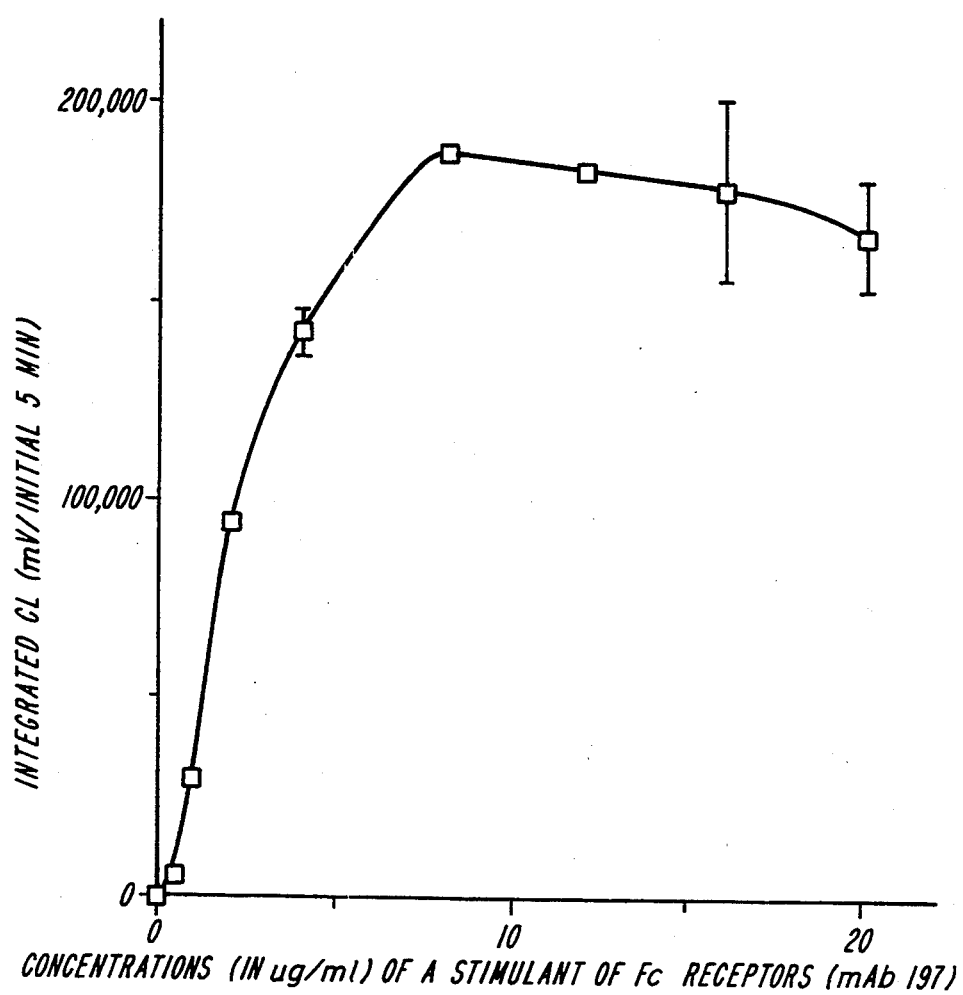
FIG. 2 is a graph showing the limits of $O_2^-$ production stimulated through Fc receptors.

The limits of $O_2^-$ production stimulated through Fc receptors: optimal stimulant concentration. 500 μM of $VO_4^{-3}$ was present. 5-10 μg/ml mAb 197 is the established maximal effective concentration in the absence of $VO_4^{-3}$ (see Pfefferkorn, L. C. and Fanger, M. W. (1989) J. Biological Chemistry 264:14112, which is incorporated by reference herein). FIG. 2 is a graph showing the resulting limits of production.

Example 3

Figure 3:
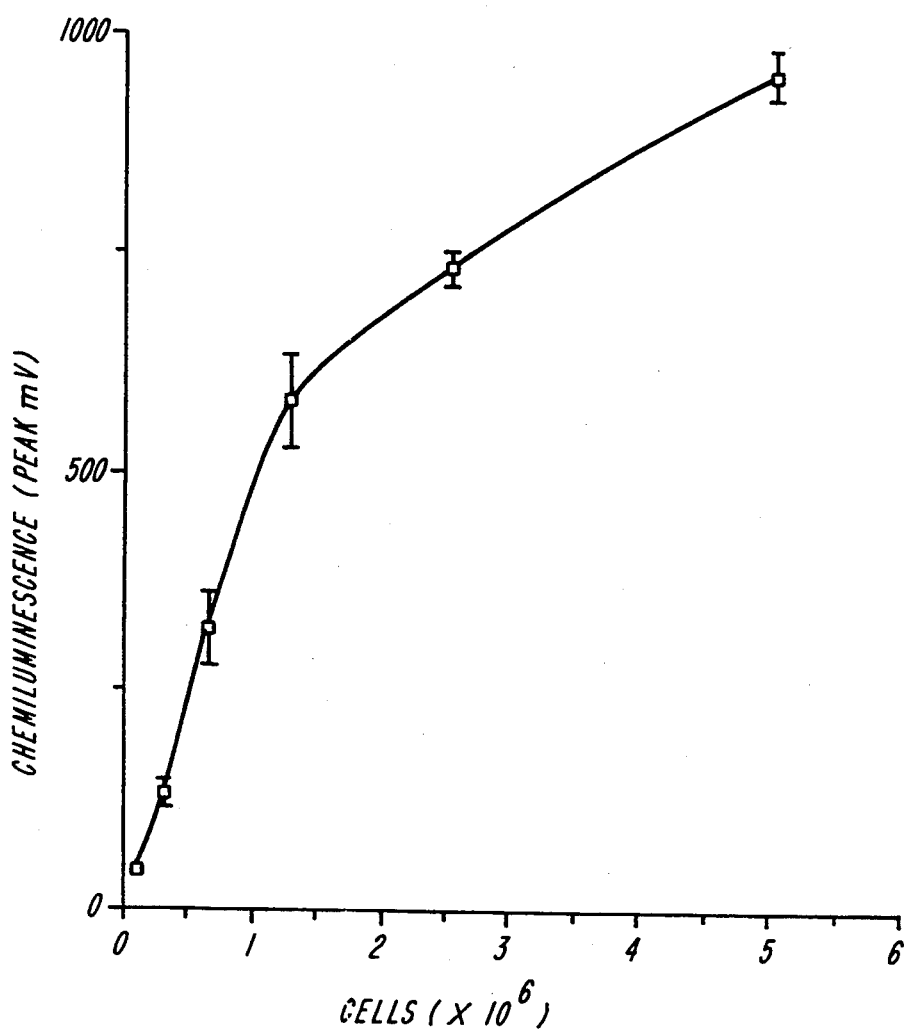
FIG. 3 is a graph showing the limited increase in sensitivity by increased cell concentrations.

FIG. 3 is a graph showing the limited increase in sensitivity by increased cell concentrations. Linear response was observed up to approximately $12 \times 10^4$ cells. Inhibition at higher concentrations due to absorption of photons by cells (self-quenching).

Example 4

Effect of $VO^{4-3}$ on the detection of $O_2^-$ stimulated by various stimulants was studied using mAb197, PMA and fMLP. TABLE 2 shows that in the presence of $VO_4^{-3}$, a substantial enhancement resulted.

TABLE 2

| 500 μM $VO_4^{-3}$ | mAb 197 | PMA | fMLP |
|---|---|---|---|
| absent | 47 ± 3 | 95 ± 9 | 2.9 ± 0.1 |
| present | 2711 ± 8 | 2182 ± 80 | 237 ± 10 |

It can be concluded that enhancement of the detection of $O_2^-$ by $VO_4^{-3}$ is independent of the type of stimulant used.

Example 5

Effect of glucose oxidase on chemiluminescence:

$O_2^-$ production is known to be dependent upon the presence of molecular oxygen. To demonstrate that $O_2^-$ is the molecule that is being detected in the unenhanced and the enhanced systems, oxygen was depleted using a standard method involving the binding of molecular oxygen to glucose by glucose oxidase. Samples that received glucose oxidase as indicated below in TABLE 3. For this data, mAb 197 was the stimulant. Data points for each sample were summed and the values are expressed in mVolts.

TABLE 3

| Glucose oxidase | $VO_4^{-3}$ (absent) | $VO_4^{-3}$ (present) |
|---|---|---|
| absent | 129 ± 2 | 10,154 ± 745 |
| present | 8.3 ± 0.2 | 112 ± 19 |
| absent, no mAb 197 | 6.0 | 16.5 |

It can be concluded that $O_2^-$ is the molecule measured by $VO_4^{-3}$ enhanced chemiluminescence. $VO_4^{-3}$ does not receive electrons from NADPH oxidase, or any intracellular component of the signaling pathway. Rather, the enhanced chemiluminescence requires the presence of oxygen indicating that $O_2^-$ is likely to be the electron donor. This possibility is pursued and shown in Example 6 below.

Example 6

Enhancement of detection by luminol-chemiluminescence of $O_2^-$ generated by xanthine oxidase and xanthine:

Xanthine oxidase oxidizes xanthine, producing $O_2^-$ as a by-product. The xanthine/xanthine oxidase (X/XO) system is cell free, being constituted by xanthine oxidase and xanthine in phosphate-buffered saline containing divalent cations and glucose. The concentration of $VO_4^{-3}$ was 500 μM. Measurements were of luminol chemiluminescence detected by an LKB luminometer. Values (in mVolts/sec) represent the sum of five time points for each sample and are expressed in mVolts.

That $O_2^-$ is the molecule produced by X/XO and detected through luminol-mediated chemiluminescence is demonstrated by the inhibition of chemiluminescence through oxygen depletion (as described in TABLE 3 above; see $VO_4^{-3}$ data below).

Orthovanadate enhances luminol-chemiluminescence in the X/XO $O_2^-$ generating system (compare $VO_4^{-3}$ (absent) with $VO_4^{-3}$ (present)). That the enhancement is of $O_2^-$ detection is demonstrated by the inhibition through oxygen depletion (glucose oxidase; see $VO_4^{-3}$ (present) data below in TABLE 4). This indicates that $VO_4^{-3}$ enhanced the detection of molecular oxygen-dependent $O_2^-$ generation.

TABLE 4

| Glucose oxidase | $VO_4^{-3}$ (absent) | $VO_4^{-3}$ (present) |
|---|---|---|
| absent | 1670 ± 58 | 12,356 ± 986 |

TABLE 4-continued

| Glucose oxidase | VO$_4^{-3}$ (absent) | VO$_4^{-3}$ (present) |
|---|---|---|
| present | 375 ± 68 | 3,073 ± 111 |

It can be concluded, therefore, that VO$_4^{-3}$ enhances the detection of O$_2^-$ generated by a cell free system composed of an enzyme and its substrate (xanthine and xanthine oxidase).

Example 7

Effect of superoxide dismutase on VO$_4^{-3}$ enhanced chemiluminescence:

Superoxide dismutase (SOD) is a scavenger of O$_2^-$, catalase hydrolyzes hydrogen peroxide, and azide blocks myeloperoxidase activity, inhibiting the production of hypochlorous acid. To determine which of these oxidants is being detected in the VO$_4$ enhanced system, monocytic cells were stimulated in the presence of each inhibitor. Chemiluminescence was measured until activity subsided. Data were summed and are expressed in mVolts.

TABLE 5

| Inhibitor | mV |
|---|---|
| none | 3948 ± 27 |
| superoxide dismutase | 87 ± 1 |
| catalase | 3051 ± 68 |
| azide | 3095 ± 70 |

It can be concluded that inhibition by SOD indicates that it is O$_2^-$ that is measured by the VO$_4^{-3}$ enhanced system.

While the invention has been described in connection with certain preferred embodiments, it is not intended to limit the scope of the invention to the particular forms set forth, but, on the contrary, is intended to cover such alternatives, modifications, and equivalents as may be included within the spirit and scope of the invention as defined by the appended claims.

I claim:

1. A method for performing an enhanced chemiluminescence assay of superoxide anion, comprising:
   (a) providing an analyte suspected of containing or of being able to generate superoxide anion;
   (b) providing a predetermined amount of a chemiluminescent substance cleavable by superoxide anion to produce a signal;
   (c) providing a predetermined amount of orthovanadate anion;
   (d) contacting the analyte with the chemiluminescent substance in (b) in the presence of the orthovanadate anion in such a manner as to permit reaction of any superoxide anion present in the analyte with the chemiluminescent substance in (b) resulting in the chemical cleavage of the chemiluminescent substance in (b) and the release of photons under conditions that are non-denaturing and non-cytotoxic to intact cells; and
   (e) measuring the photons released in step (d).

2. The method of claim 1, wherein the chemiluminescent substance is selected from the group consisting of luminol and isoluminol 3. The method of claim 1, wherein the orthovanadate anion is present in an aqueous solution at a concentration of from 0.01 to 2.5 mM.

4. The method of claim 1, wherein the orthovanadate anion is present in an aqueous solution at a concentration of from 1.0 to 2.5 mM.

5. The method of claim 1, wherein the orthovanadate anion is present in an aqueous solution at a concentration of from 1.5 to 2.0 mM.

6. The method of claim 1, wherein the analyte is selected from the group consisting of phagocytes, monocytes, polymorphonuclear leukocytes, and macrophages.

7. The method of claim 1, wherein the orthovanadate anion is present as an orthovanadate salt.

8. The method of claim 7, wherein the orthovanadate salt is selected from the group consisting of potassium orthovanadate and sodium orthovanadate.

9. A kit for performing an enhanced chemiluminescence assay of superoxide anion, comprising the following components in separate containers:
   (a) a predetermined amount of orthovanadate anion has been inserted after "comprising"; in line 3 under conditions that are non-denaturing and non-cytotoxic to intact cells; and
   (b) a predetermined amount of a chemiluminescent substance cleavable by superoxide anion to produce a signal.

10. The kit of claim 9, wherein the chemiluminescent substance is selected from the group consisting of luminol and isoluminol.

11. The kit of claim 9, wherein the orthovanadate anion is present in an aqueous solution at a concentration of from 0.0 1 to 2.5 mM.

12. The kit of claim 9, wherein the orthovanadate anion is present in an aqueous solution at a concentration of from 1.0 to 2.5 mM.

13. The kit of claim 9, wherein the orthovanadate anion is present as an orthovanadate salt.

14. The kit of claim 13, wherein the orthovanadate salt is selected from the group consisting of potassium orthovanadate and sodium orthovanadate.

15. The kit of claim 13, wherein the orthovanadate salt is provided in concentrated form.

16. The kit of claim 13, wherein the orthovanadate salt is provided in lyophilized form.

* * * * *

UNITED STATES PATENT AND TRADEMARK OFFICE
CERTIFICATE OF CORRECTION

PATENT NO. : 5,401,640
DATED : March 28, 1995
INVENTOR(S) : Lorraine C. Pfefferkorn It is certified that error appears in the above-indentified patent and that said Letters Patent is hereby corrected as shown below:

In the Claims:

In claim 9, column 10, line 31, delete "has been inserted after "comprising"; in line 3."

Signed and Sealed this

Twenty-ninth Day of August, 1995

Attest:

BRUCE LEHMAN

Attesting Officer        Commissioner of Patents and Trademarks